United States Patent [19]

Ringwald

[11] 4,333,945
[45] Jun. 8, 1982

[54] THIAZOLINE AND IMIDAZOLINE DERIVATIVES USEFUL AS MINOR TRANQUILIZERS

[75] Inventor: Erwin Ringwald, Riehen, Switzerland

[73] Assignee: Sandoz Ltd., Basel, Switzerland

[21] Appl. No.: 212,661

[22] Filed: Dec. 3, 1980

Related U.S. Application Data

[63] Continuation-in-part of Ser. No. 185,943, Sep. 10, 1980, abandoned, which is a continuation of Ser. No. 121,128, Feb. 13, 1980, abandoned.

[30] Foreign Application Priority Data

Feb. 16, 1979 [GB] United Kingdom ................. 7905543
Feb. 16, 1979 [GB] United Kingdom ................. 7905544

[51] Int. Cl.$^3$ .......................................... A61K 31/425
[52] U.S. Cl. .................................................. 424/270
[58] Field of Search ......................................... 424/270

[56] References Cited

PUBLICATIONS

Neurology 28(2) Sep. 1978, Bauer.
Abstract No. 66–11th World Congress of Neurology, Amsterdam, Sep. 11–16, 1977.
Nervenarzt 48 351–354 & 355–358 (1977).

*Primary Examiner*—Stanley J. Friedman
*Attorney, Agent, or Firm*—Gerald D. Sharkin; Robert S. Honor; Joseph J. Borovian

[57] ABSTRACT

This invention provides a new tranquillizing use of thiazoline and imidazoline derivatives and novel pharmaceutical compositions for such use.

4 Claims, No Drawings

THIAZOLINE AND IMIDAZOLINE DERIVATIVES USEFUL AS MINOR TRANQUILIZERS

This is a continuation-in-part of application Ser. No. 185,943 filed Sept. 10, 1980, which in turn is a continuation of application Ser. No. 121,128 filed Feb. 13, 1980, both now abandoned.

The present invention relates to a novel pharmaceutical use of compounds of formula I,

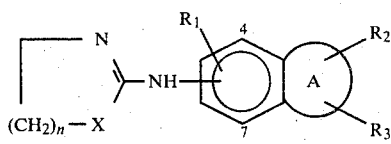

wherein

X is sulphur or imino, n is 1 or 2, $R_1$ is hydrogen, halogen, alkyl($C_{1-4}$), alkylthio($C_{1-4}$), alkoxy($C_{1-4}$), trifluoromethyl or hydroxy, A is a five-membered heterocyclic ring containing at least one heteroatom chosen from nitrogen, oxygen and sulphur and having 2 adjacent carbon atoms common with the benzene ring, with the proviso that the nucleus is other than benzo-2,1,3-thiadiazole, and $R_2$ and $R_3$ are substituents which may be present in ring A, wherein $R_2$ is attached to a ring carbon atom and is hydrogen, halogen, alkyl($C_{1-4}$), alkoxy($C_{1-4}$), alkylthio($C_{1-4}$), trifluoromethyl or hydroxy and $R_3$ is attached to a ring nitrogen atom and is hydrogen or alkyl($C_{1-4}$), with the proviso that, when A is [c]pyrrole, the nitrogen atom of A is substituted by alkyl($C_{1-4}$), and of compounds of formula I',

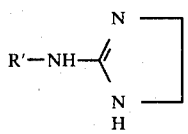

wherein either
(i) R' is a radical of formula II,

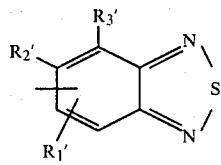

wherein each of $R_1'$, $R_2'$ and $R_3'$, independently, is hydrogen, halogen, alkyl($C_{1-4}$), alkoxy($C_{1-4}$), nitro, cyano, hydroxy or alkylthio($C_{1-4}$), or (ii) R' is a radical of formula III,

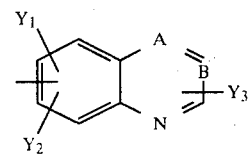

wherein
either each of A and B is =CH—, or one of A and B is =CH— and the other of A and B is =N—, $Y_1$ and $Y_2$, independently, are hydrogen, halogen, alkyl($C_{1-4}$), alkoxy($C_{1-4}$), nitro, trifluoromethyl, cyano, hydroxy or alkylthio($C_{1-4}$), and $Y_3$ is hydrogen, alkyl($C_{1-4}$) or alkoxy($C_{1-4}$).

The compounds of formula I are in general known, e.g. from DOS No. 2800062, DOS No. 2653005 and DOS No. 2416024. The compounds have been stated to have diverse pharmacological activities, e.g. myotonolytic activity. The compounds of formula I', wherein R' is a radical of formula II are also in general known. They are disclosed in U.S. Pat. No. 3,843,668 and DOS No. 2636309 and said to be useful as anti-tremor and anti-rigor agents. The compounds of formula I', wherein R' is a radical of formula III are, in general, known e.g. from U.K. Patent Specification No. 1 381 979 and said to be active as antihypertensives. We have now surprisingly found that the above compounds of formula I and I' exhibit tranquilizing activity e.g. for the treatment of neuroses. The compounds act thus as effective minor tranquillisers. This treatment of neuroses is to be distinguished from the treatment of psychoses or schizophrenia (a major tranquillizing effect) on the one hand and from physical sedation of normal subjects resulting in tiredness which can be observed as a side effect of many drugs on the other hand.

In the compounds of formula I A is, for example, [b] or [c]pyrrole, [d]imidazole, [d]pyrazole, [d]triazole, [b] or [c]furan, [c] or [d]isoxazole, [d]oxazole, [c]furazan, [b] or [c]thiophene, [c] or [d]isothiazole, [d]thiazole, [d](1,2,3)-thiadiazole, [b] or [c]pyrroline, [b] or [c]dihydrofuran or [b]dihydrothiophene. Preferably A is [b]furan, [b]thiophene, [d]oxazole or [d]triazole, especially [b]furan. Halogen means fluorine, chlorine, bromine or iodine, preferably bromine or chlorine. Alkyl, alkoxy or alkylthio preferably contains 2 carbon atoms, especially 1 carbon atom. $R_1$ is preferably other than hydroxy and is preferably hydrogen, chlorine or methyl. $R_1$ is preferably ortho to the heterocyclic-amino moiety. $R_2$ is preferably alkyl, hydrogen or halogen, especially chlorine. The heterocyclic-amino residue is preferably attached to position 4 or 7 of the bicyclic moiety. When the heterocyclic-amino moiety is attached to the 4 position of the bicyclic moiety, then $R_2$, when present, is preferably in the 3 position. $R_2$, when present, is preferably alkyl. n is preferably 1.

Examples of compounds of formula I are: 4-methyl-5-(2-thiazolin-2-yl-amino)-indazole, 4-chloro-5-(2-thiazolin-2-yl-amino)-indazole, 6-chloro-5-(2-thiazolin-2-yl-amino)-indazole and 6-methyl-5-(2-thiazolin-2-yl-amino)-indazole.

In the compounds of formula I' any carbon containing substituent has especially 1 carbon atom.

Halogen is preferably fluorine, chlorine or bromine.

Preferred examples of formula I', where R' is a radical of formula II, are those of formula I'a,

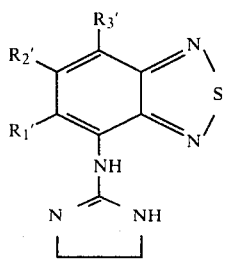

wherein each of $R_1'$, $R_2'$ and $R_3'$, independently, is hydrogen, halogen, alkyl($C_{1-4}$), alkoxy($C_{1-4}$), nitro, cyano, hydroxy or alkylthio($C_{1-4}$), especially 5-chloro-4-(2-imidazolin-2-yl-amino)-2,1,3-benzothiadiazole.

Preferred examples of formula I', where R' is a radical of formula III, are those compounds wherein $Y_1$ is halogen, especially chlorine or bromine, and $Y_2$ and $Y_3$ are hydrogen, e.g. 5-bromo-and 5-chloro-6-(2-imidazolin-2-yl-amino)-quinolines and -quinoxalines and 8-bromo-7-(2-imidazolin-2-yl-amino)-quinazoline and -quinoline.

The tranquillizing activity of the compounds is indicated in clinical trials and in standard animal tests. For example, in a double-blind clinical trial a significant tranquillizing effect was observed according to a 20-symptom scale following the method of Mehnert when a compound of formula I', e.g. 5-chloro-4-(2-imidazolin-2-ylamino)-2,1,3-benzothiazole, was administered orally in the form of unit dosage three times a day at a daily dose of 3 and 6 mg per day over 14 days to subjects suffering from neuroses with hypochondrial symptoms and psychosomatic disorders. The results were registered with the Mehnert 20-symptom therapy scale before the trial and on the third, sixth, tenth and forteenth day of the therapy.

The tranquillizing activity of the compounds of formula I and I' is confirmed in standard animal tests. Thus the compounds suppress motility as can be demonstrated in mice. In one test two groups, each comprising four mice (one group as a control group), administered with 0.01 mgkg to 0.1 mg/kg p.o. of the test compound is placed in a cage in redlight (Electronic Motility Testing obtainable from Motron-Producter, Stockholm, Sweden). The number of times the mice interrupt the light beams is counted alectronically every fifteen minutes over a period of 60 minutes.

Furthermore, the compounds reduce defensive ambivalence behaviour (a form of conflict behaviour) and increase social contact in standard animal introduction tests. In one test a male mouse administered with 0.1 to 1 mg/kg p.o. of the compound is placed for 6 minutes into the home cage of an isolated, aggressive male mouse. The behaviour of the introduced mouse is then statistically analysed in particular noting the frequency and duration of various acts and postures, e.g. non-social activity, social investigation and mating, aggression, defensive ambivalence, fleeing or retreating and feeding behaviour, according to the method of A. K. Dixon and J. H. Mackintosh, Anim. Behav. 19, 138–140 (1971) using the behavioural categories outlined by A. K. Dixon "Rodent Social Behaviour in Relation to Biomedical Research" in "Das Tier im Experiment", Ed. W. Weihe, Hans Huber Verlag, Bern 1978.

Furthermore, on administration of 0.3 to 3 mg/kg p.o. of the compounds to rats in the sleep/wake cycle carried out in accordance with the principles of H. Kleinlogel et al., European J. Pharmacol. 33, 159–163 (1975) an increase of dozing is observed. The EEG was recorded over 8 hours.

The above compounds are therefore useful as tranquillizers for the treatment of neurotic subjects.

For the above mentioned novel use the dosage will, of course, vary depending on the compound employed, mode of administration and therapy desired. However, in general, satisfactory results are obtained with a daily dosage of from about 0.01 to about 3 mg per kg animal body weight (e.g. from 0.01 to 1 mg/kg), conveniently given in divided doses 2 to 4 times a day or in sustained release form. For the larger mammal, the total daily dosage is in the range from about 0.25 to about 16 mg, conveniently administered in divided doses 2 to 4 times a day in unit dosage form containing from about 0.125 mg to about 8 mg of the compound admixed with a solid or liquid pharmaceutical carrier or diluent.

For 5-chloro-4-(2-imidazolin-2-yl-amino)-2,1,3-benzothiadiazole the total daily dosage is conveniently from 1 to 12 mg, preferably from 2 to 8 mg.

The compounds may be administered in free base form or in pharmaceutically acceptable acid addition salt form. Such salt forms are known and include for example the hydrochloride. The free base forms and said acid addition salt forms exhibit the same order of activity.

The compounds may be administered orally as pharmaceutical compositions in the form of tablets, powders, granules, capsules, suspensions, sirups and elixirs, or parenterally in the form of injectable solutions or suspensions. Aside from the compound of formula I or I' the compositions may contain pharmaceutically inert organic or inorganic adjuvants, optionally granulating agents, binding agents, lubricants, dispersing agents, wetting agents and preservatives. Moreover, the pharmaceutical compositions may contain colouring, flavouring and sweeting substances, etc. Adjuvants for the production of tablets may be calcium carbonate, lactose, microcrystalline cellulose, mannitol, or talc. Starch and alginic acid or microcrystalline cellulose may be used as granulating and disintegrating agents, starch, polyvinylpyrrolidone and gelatine may be used as binding agents, and magnesium stearate, stearic acid, colloidal silicon dioxide and talc as lubricants. Tablet formulations may be coated or uncoated, with the coating being applied in a manner per se and having the purpose of delaying the disintegration and adsorption in the gastrointestinal tract, thus providing a retarded effect over a longer period. Suitable suspending agents for the production of liquid administration forms are especially methyl cellulose, tragacanth and sodium alginate. Suitable wetting agents are e.g. polyoxyethylene stearate and poloxyethylene sorbitanmonooleate. Furthermore, preservatives such as p-hydroxy-benzoic acid alkyl ester may be used. Capsule formulations may contain the compound of formula I or I' on its own or together with an inert solid diluent, for example calcium phosphate, starch, lactose, mannitol, colloidal silicon dioxide and microcrystalline cellulose.

Solid preparations are preferred, especially hard-filled capsules and tablets, for reasons of easier production and favourable administration.

The invention also provides a pack containing a pharmaceutical composition containing a compound of formula I or I' together with instructions for use as a tranquillizer or sedating agent.

Other preferred compounds include 4-bromo-5-(2-imidazolin-2-yl-amino)-2,1,3-benzothiadiazole.

The following Examples are illustrative of compositions for use in the invention.

EXAMPLE 1

Tablet suitable for oral administration

Tablets containing the ingredients indicated below may be prepared by conventional techniques and are administered at a dose of two tablets four times a day.

| Ingredient | Weight (mg) |
| --- | --- |
| 5-chloro-4-(2-imidazolin-2-yl-amino)-2,1,3-benzothiadiazole hydrochloride (active agent) | 1.144 mg (= 1.0 mg base) |
| Lactose | 55.0 mg |
| Microcrystalline cellulose | 51.656 mg |
| Colloidal silicon dioxide | 0.2 mg |
| Stearic acid | 2.0 mg |
| | 110.0 mg |

If desired the tablet may be shaped so that it may be easily divided into two.

EXAMPLE 2

Capsule suitable for oral administration

Capsules containing the ingredients indicated below may be prepared by conventional techniques and are administered at a dose of one capsule two to four times a day.

| Ingredient | Weight |
| --- | --- |
| 5-chloro-4-(2-imidazolin-2-yl-amino)-2,1,3-benzothiadiazole hydrochloride | 1.144 mg (≃ 1 mg base) |
| Lactose | 174.356 mg |
| Corn starch | 120.0 mg |
| Colloidal silicon dioxide | 1.5 mg |
| Magnesium stearate | 3.0 mg |
| | 300.0 mg |

EXAMPLE 3

Sterile solution for injection

A solution for injection containing the ingredients indicated below may be prepared by conventional techniques including buffering as indicated below and subsequent sterilizing in conventional manner. The solution may be injected once a day.

| Ingredient | Weight/Volume |
| --- | --- |
| 5-chloro-4-(2-imidazolin-2-yl-amino)-2,1,3-benzothiadiazole hydrochloride (active agent) | 3.432 mg/ml (~ 3.0 mg base) |
| Sodium chloride | 7.000 mg/ml |
| Acetic acid conc. | 0.950 mg/ml |
| Sodium acetate trihydrate | 2.380 mg/ml |
| Distilled water | to 1 ml |
| Buffer to pH 5 | |

If desired the solution may be sealed into ampoules.

What we claim is:

1. A method of tranquilizing a neurotic subject which comprises administering to said subject a therapeutically effective amount of a compound of formula I' a

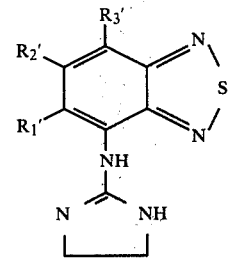

wherein each of $R_1'$, $R_2'$ and $R_3'$, independently, is hydrogen, halo, $C_{1-4}$ alkyl, $C_{1-4}$ alkoxy, nitro, cyano, hydroxy or $C_{1-4}$ alkylthio, said compound being in free base or in pharmaceutically acceptable acid addition salt form.

2. A method according to claim 1 wherein the compound is 5-chloro-4-(2-imidazolin-2-yl-amino)-2,1,3-benzothiadiazole.

3. A method according to claim 1 wherein the compound is administered at a daily dosage of from 0.25 to 16 mg.

4. A method according to claim 2, wherein the compound is administered in unit dosage form containing from about 0.125 mg to about 8 mg.

* * * * *